United States Patent
Katerkamp et al.

(10) Patent No.: US 6,440,748 B1
(45) Date of Patent: Aug. 27, 2002

(54) PROCESS AND DEVICE FOR CARRYING OUT FLUORESCENCE IMMUNOASSAYS

(75) Inventors: Andreas Katerkamp, Münster; Ulrich Kunz, Biberach; Frank Grawe, Münster; Göran Key, Osnabrück, all of (DE)

(73) Assignee: Institut für Chemo- und Biosensorik Münster E.V. (DE)

( * ) Notice: Subject to any disclaimer, the term of this patent is extended or adjusted under 35 U.S.C. 154(b) by 0 days.

(21) Appl. No.: 09/530,505

(22) PCT Filed: Oct. 27, 1998

(86) PCT No.: PCT/DE98/03154

§ 371 (c)(1), (2), (4) Date: Jul. 18, 2000

(87) PCT Pub. No.: WO99/22222

PCT Pub. Date: May 6, 1999

(30) Foreign Application Priority Data

Oct. 28, 1997 (DE) .......................... 197 47 572

(51) Int. Cl.⁷ .................... G01N 21/00; G01N 33/543; G01N 33/00; G01N 21/17; C12M 3/00
(52) U.S. Cl. .................... 436/518; 436/172; 436/283.1; 436/501; 436/536; 436/805; 435/7.1; 435/7.72; 435/7.9; 435/7.92; 435/7.94; 435/287.1; 435/287.3; 435/288.5; 435/288.7; 435/808; 356/73.1; 356/319; 356/320; 356/349; 422/50; 422/52; 422/58; 422/59; 422/68.1; 422/82.08; 422/82.11; 422/82.05
(58) Field of Search .............................. 422/50, 52, 58, 422/59, 68.1, 82.08, 82.11, 82.05; 435/7.1, 7.72, 7.9, 7.94, 7.92, 287.1, 287.3, 288.5, 288.7, 808; 436/501, 536, 283.1, 805, 518, 172; 356/73.1, 319, 320, 349

(56) References Cited

U.S. PATENT DOCUMENTS

| | | | | |
|---|---|---|---|---|
| 3,950,101 A | * | 4/1976 | Dewey, Jr. .................... | 356/51 |
| 4,076,420 A | * | 2/1978 | De Maeyer et al. .......... | 356/73 |
| 4,155,007 A | * | 5/1979 | Beckmann .................... | 250/253 |
| 4,608,344 A | * | 8/1986 | Carter et al. .................. | 436/34 |
| 4,775,637 A | * | 10/1988 | Sutherland et al. .......... | 436/527 |
| 4,909,990 A | | 3/1990 | Block et al. .............. | 422/82.11 |
| 5,032,714 A | * | 7/1991 | Takahashi et al. ........... | 250/213 |
| 5,077,012 A | | 12/1991 | Guirguis ....................... | 422/58 |
| 5,237,631 A | * | 8/1993 | Gavish et al. ................. | 385/12 |
| 5,340,715 A | * | 8/1994 | Slovacek et al. .............. | 435/6 |
| 5,492,674 A | | 2/1996 | Meserol ................... | 422/82.08 |

FOREIGN PATENT DOCUMENTS

| | | |
|---|---|---|
| DE | 3446756 C1 | 12/1984 |
| DE | 4294539 T1 | 12/1992 |
| DE | 19546535 A1 | 12/1995 |

OTHER PUBLICATIONS

International Publication No.: WO 97/10506, published Mar. 20, 1997 for International Application No. PCT/US96/13812.

* cited by examiner

*Primary Examiner*—Bao-Thuy L. Nguyen
*Assistant Examiner*—Kartic Padmanabhan
(74) *Attorney, Agent, or Firm*—Young & Basile, P.C.

(57) ABSTRACT

The invention concerns a device and a method for carrying out fluorescence immunoassays, wherein from at least one light source light is directed onto a surface at one end of a light waveguide and with the light coupled into the light waveguide by evanescent field excitation at the surface of the light waveguide fluorescence of at least one labelling substance bound to a chemical or biochemical partner of a general receptor-ligand system is excited. The solution according to the invention is here to provide a possible way of carrying out fluorescence immunoassays with high accuracy of measurement at low cost and within a short time. To achieve this object, the fluorescent light is decoupled from the light waveguide and directed via an optical system onto an optical detector with which the intensity of the fluorescent light is measured. Here the light waveguide is held in a measuring chamber formed in a piston of a piston and cylinder unit, and the measuring chamber is connected to the interior of the cylinder by an inlet formed in the piston.

22 Claims, 6 Drawing Sheets

PROCESS AND DEVICE FOR CARRYING OUT FLUORESCENCE IMMUNOASSAYS

The subject application claims priority of Intentional Application PCT/DE98/03154 filed on Oct. 27, 1998 and German foreign application 197 47 572.8 filed on Oct. 28, 1997.

BACKGROUND OF THE INVENTION

The invention concerns a device and a method for carrying out fluorescence immunoassays, wherein from at least one light source light is directed onto a surface at one end of a light waveguide and with the light coupled into the light waveguide by evanescent field excitation at the surface of the light waveguide fluorescence of at least one labelling substance bound to a chemical or biochemical partner of a general receptor-ligand system is excited and the fluorescent light is partially coupled into the light waveguide and decoupled from the light waveguide from. the surface into which the exciting light was coupled and directed via an optical system onto an optical detector with which the intensity of the fluorescent light is measured.

With the invention the most varied biochemical assays can be carried out on general receptor-ligand systems such as erg. antibody-antigen. With the assays, chemical or biochemical substances are analysed quantitatively in liquid samples.

Thus antibodies can be labelled with a given labelling substance (fluorogens), wherein the respective labelling substance can be optically excited at a given exciting wavelength of the light, and the fluorescent light which is obtained by excitation and which in turn occurs with another wavelength is detected with a suitable optical detector and the intensity of the fluorescent light is used to determine the respective proportion of the chemical or biochemical substance from the sample liquid. For fluorescence excitation, the evanescent field which forms at an interface is used. Here, the known physical relationships of the evanescent field and at the same time in particular the necessary total reflection of the exciting light must be taken into consideration.

Thus from WO 97/10 506 is known an optical device for carrying out fluorescence immunoassays in which is used a light waveguide into which light from a light source is coupled and fluorescence of a sample is produced by evanescent field excitation. Here, the surface of the light waveguide before carrying out the respective assay, that is, introducing the sample liquid into a receptacle in which the light waveguide is also contained, is coated accordingly with a chemical or biochemical component.

For coupling the light into the light waveguide, a very elaborate and complicated optical system which consists of a plurality of individual optical components is necessary. Thus the light from the light source used is directed via a lens system onto a semi-transparent mirror and a portion of the light is coupled as a reference signal onto an optical detector and the other portion of the light is coupled via an additional lens into the fibre. In this case the end of the light waveguide opposite the coupling and decoupling surface is metallised, so that most of the exciting and fluorescent light is decoupled from the light waveguide again. As a result, the ratio of exciting to fluorescent light for evaluation with the photodetector is made worse and consequently the accuracy of measurement is undesirably impaired.

Another drawback of this known device lies in that the light is to pass through the lens arranged in front of the coupling surface of the light waveguide, so that light incidence at a precise main angle within a narrow angular range into the light waveguide which is advantageously required for evanescent field excitation can be achieved only with great difficulty, if at all.

The fluorescence immunoassays are then carried out according to this known solution in such a way that the prepared, coated light waveguide contained in the receptacle is brought into contact with the sample liquid by the fact that the sample liquid enters through perforations in the lid of the receptacle and binding to the complementary partner of the receptor-ligand system which is immobilised on the surface of the light waveguide can be effected. After binding, fluorescence is excited by irradiation of the light from the light source used and its intensity is measured with the optical detector.

Since for the binding process the respective transport of substances to the light waveguide surface is important and in this case convection and diffusion must be taken into consideration, in the solution known from WO 97/10 506 measurement errors occur because the sample volume respectively contained in the receptacle is constant and entry of the sample liquid through the perforations takes place very rapidly and hence binding is effected in a stationary liquid. In this case binding is influenced mainly by diffusion, which apart from other drawbacks also leads to prolonging the measuring time.

With this type of measurement without time resolution, background correction of the measurement signal is necessary, which was not taken into consideration in WO 97/10506.

Another essential drawback which is associated with this known solution lies in that only the exciting light is used as the reference signal in order to increase the accuracy of the measurement results. To improve the measurement accuracy and informativeness of the assay results as well as increased reproducibility, however, it is necessary to perform reference measurements more suitable for the immunoassays.

Furthermore in U.S. Pat. Nos. 4,909,990 and 5,492,674 are described solutions with which fluorescence immunoassays can be carried out. Here there is used a light waveguide transparent to exciting and fluorescent light, for example an optical fibre, which is at least partially guided in a capillary sleeve or held therein. Before carrying out the fluorescence immunoassay, a sample liquid passes into the gap between capillary sleeve and light waveguide, which has been suitably prepared biochemically beforehand and is held there. Transport of substances to the surface of the light waveguide is here effected almost entirely by diffusion, and after the capillary sleeve is suitably filled and the sample liquid has been brought into contact with the prepared surface of the light waveguide in the region of the capillary sleeve measurement of the fluorescent light is effected, which has been excited in a conventional manner by using the evanescent field of exciting light radiated into the light waveguide. A relatively small sample volume can be used owing to the small usable volumes of the capillary.

SUMMARY OF THE INVENTION

It is therefore the object of the invention to provide a possible way of carrying out fluorescence immunoassays with high accuracy of measurement at low cost within a short time.

The device according to the invention is based on the known state of the art already described and also uses at least one light source with which light, for fluorescence excitation by means of the evanescent field, is coupled into a light waveguide, and the intensity of the fluorescent light of a labelling substance which is bound to a partner of a general receptor-ligand system is determined with an optical detector. Here the fluorescent light and part of the exciting light are decoupled from the same surface into which the exciting light was coupled. The light waveguide is here held in a measuring chamber which is formed in a piston of a piston and cylinder unit. The measuring chamber of the piston here has an inlet, into the interior of the cylinder, which passes through the piston. Such a piston and cylinder unit can here be at least approximately constructed as a conventional syringe, wherein only the piston must be modified correspondingly with the measuring chamber.

A further improvement can be achieved by the fact that in the piston is formed an additional sample collecting chamber which communicates with the measuring chamber. This results in a unit in which incubation and measurement can be performed and after carrying out the respective assay the sample is reliably held and the corresponding piston and cylinder unit can be transported and disposed of without major problems or risk.

The light waveguide may comprise, on the side on which the exciting light is coupled and the fluorescent light and part of the exciting light are decoupled again, a surface which closes the piston in this direction. It therefore also forms a closure for measuring and sample collecting chambers. Moreover it serves to fix the light waveguide on this side of the piston. Here the light waveguide and the surface can advantageously be made in one piece from the same material such as for example a polymer such as polymethylmethacrylate (PMMA).

At the other end of the light waveguide is advantageously arranged a light absorber which is preferably made of a black-coloured plastic. Here the light absorber can be dimensioned and shaped so as to align and fix the light waveguide in the lower region of the measuring chamber.

With the light absorber can be obtained a further favourable effect which improves the ratio of exciting and fluorescent light to a value favourable to measurement. By means of the light absorber nearly all of the exciting light is absorbed, while the fluorescent light is only reduced by half, so that the ratio of the two light fractions is shifted in favour of the fluorescent light. Thus very sensitive light detectors can be used to measure the weak fluorescent light.

It is also possible to divide the light waveguide into several light wave-conducting segments running parallel to light propagation in the light waveguide. The individual segments are here spatially separated from each other by a thin layer. The refractive index $n_2$ of this layer is less than that of the light wave-conducting segments, in order to achieve light conduction by total reflection. Multi-substance measurement is possible with such a segmented light waveguide, because a fluorescence immunoassay can be carried out with each light wave-conducting segment.

For carrying out the assays it is moreover favourable to provide a closable opening in the surface which closes the piston, wherein the closure may be e.g. a thin film or a corresponding plug which when required, which will be returned to later, can be removed and the opening released.

The respective sample liquid can favourably be supplied via an inlet opening in the cylinder, as is also the case with conventional syringes.

Here the inlet opening should favourably be closable with a valve, to avoid unwanted escape of sample liquid from the cylinder, after filling it.

A further favourable embodiment of the device according to the invention uses an absorbent material which is at least contained in the sample collecting chamber, wherein part of the absorbent material can also extend into the measuring chamber.

In front of or in the above-mentioned inlet through the piston into the measuring chamber there can be filters and/or an immunocolumn and/or a membrane which can be permeable or semi-permeable, in order to be able to keep certain components contained in the sample liquid away from measurement or, directed otherwise, to influence the measurement with the use of an immunocolumn and/or membrane and/or the filter.

The various fluorescence immunoassays can now be carried out in such a. way that the surface of the light waveguide is coated with different chemical or biochemical components such as e.g. antibodies, wherein coating can be effected for example in a two-stage batch process. This batch process includes, in addition to coating by e.g. adsorptive immobilisation of the respective components, prior cleaning of the light waveguide surface. This can be carried out in an ordinary immersion process by which it is easy and effectively possible to simultaneously treat a relatively high number of such light waveguides. As the light waveguides can also be made by conventional injection moulding methods and hence a large number of light waveguides are available joined together after injection moulding, this operation can of course be performed extremely effectively.

The light waveguides coated in this way are then inserted in the measuring chamber of a piston constructed as already described, wherein the opening in the surface at one end of the light waveguide which closes the piston is also closed. Connection of this surface to the piston can then be effected by gluing, wherein an airtight closure is to be secured.

There is also the possibility of covering the face of the piston used before introduction into the cylinder, e.g. with a biocomponent.

Alternatively the surface of the inside of the cylinder can also be covered with a freeze-dried biocomponent. Covering the surface of the inlet of the cylinder is also suitable.

In the form prepared in this way, the device according to the invention can be made available for the respective requirements, wherein longer storage times under appropriate conditions are quite possible too.

The piston and cylinder unit prepared in this way can then if required be drawn up like a syringe and filled with sample liquid, wherein a precise quantity of sample liquid can be drawn into the cylinder. The sample liquid remains exclusively in the cylinder and cannot pass through the inlet in the piston into the measuring chamber and hence also into the sample collecting chamber, as the air contained therein cannot be displaced because the opening which allows escape of air is still closed.

On covering the inlet of the cylinder and/or the cylinder surface and/or the piston face with biocomponents, the latter enter the sample liquid during filling. In the process there is a reaction (preincubation) of the biocomponent with the chemical or biochemical components of the sample liquid. After this preincubation the correspondingly pretreated sample can be conducted into the measuring chamber and there past the light waveguide when the air outlet opening in the end face is open. This can be effected, in the case of a film used for this purpose, by removing or piercing it. The air from the measuring chamber and sample collecting chamber can escape and the chambers are filled by capillary forces, wherein the sample liquid flows continuously past the light waveguide surface. Flow of the sample liquid through the measuring chamber at a predefined flow rate can also be achieved by correspondingly directed movement of the cylinder, with the syringe piston fixed. Here too it is not absolutely essential for the air outlet opening in the end face to be open, as the air in the measuring chamber and particularly in the sample collecting chamber can be compressed and so the sample can also flow past the light waveguide surface. With this manner of operation, an air outlet opening in the end face is not necessary.

During flow of the preincubated sample liquid through the measuring chamber, the syringe piston must be held precisely so that the light from the light source for the exciting light impinges at the correct angle on the surface and can be coupled into the light waveguide. If a light waveguide with a diameter of approx. 1 mm is used, relatively large reductions can be made on the accuracy of position without the respective measurement results being adversely affected.

The above-mentioned valve at the inlet into the cylinder prevents the sample liquid contained in the cylinder from escaping again undesirably and the whole quantity can be used for the measurement, which is particularly important when the cylinder is moved for flow through the measuring chamber. During flow of the sample liquid through the measuring chamber and binding of the labelled chemical or biochemical component to the partner of the receptor-ligand system immobilised on the light waveguide surface, the fluorescent light which is excited by means of the above-mentioned light source and which is decoupled from the end face of the light waveguide is detected with the above-mentioned optical detector and its intensity measured. The optical structure to be used for this will be further specified later.

But another improved possibility for conduction of the sample liquid, preincubated as described, past the light waveguide through the measuring chamber can also be effected in such a way that in the sample collecting chamber is contained a material which is highly absorbent to liquid, such as e.g. fleece. This material extends into the measuring chamber, and the preincubated sample liquid can pass out of the cylinder after opening the closure of the opening present in the surface, by capillary force into the measuring chamber, and is further conducted by capillary forces in the liquid-absorbing material through the measuring chamber until the sample collecting chamber is full. This leads to more stable liquid transport.

Here too, measurement of the fluorescence intensity is effected in the period in which the sample liquid flows along the light waveguide through the measuring chamber. If a device constructed in this way is used, the above-mentioned valve at the inlet into the cylinder can be dispensed with, so that for example a conventional syringe main body which is available cheaply can be used as the cylinder.

On binding to a biochemically sensitised surface, allowance must be made for two different effects in a flowing system, namely convection and diffusion.

It is known from hydrodynamics that, starting from laminar flow, the flow rate of a fluid in a pipe or channel-like structure such as is the measuring chamber constructed according to the invention is variable with the distance from the wall. Here the flow rate directly at the wall is 0 and increases with increasing distance from the wall.

Taking this fact into account, two layers can be defined in such a laminar or quasi-laminar flow as occurs reliably with the device according to the invention. These are firstly a hydrodynamic layer at a given distance from the wall, and secondly a diffusive layer, the respective distances from the layers to the wall being dependent on the viscosity and flow rate of the fluid.

Above the diffusive layer, that is, at a greater distance from the wall, the chemical and biochemical components are moved towards the surface by convection, and within the diffusive layer, i.e. in a direction towards the wall, movement is then effected by diffusion processes. Mass transport by convection is substantially greater than that which can be achieved by diffusion. This means for the relatively rapid antigen-antibody reaction that the reaction process is greatly slowed down by the relatively slow diffusion process, and this can lead to for example a time of approx. 1 h being needed for an immunoassay in order to determine a sufficiently accurate measurement result.

In case of diffusive transport of substances, a further rebinding of already bound chemical or biochemical components occurs with a high probability, which, like the fact that the concentration of substances is higher within the flow than in the region of the diffusive layer, falsifies the measurement result.

By increasing the flow rate of the fluid, the thickness of the diffusive layer can be reduced and so the effect of convective transport of substances to the wall at which the chemical or biochemical components are to be bound is increased. Hence the response behaviour of the immunoassay is greatly improved and consequently the necessary measuring time is reduced.

But as an alternative to increasing the flow rate, with a non-elevated flow rate too the thickness of the channel-like throughflow can be decreased in order to reduce the extent of the diffusive layer, such as can be designed advantageously with the arrangement according to the invention consisting of measuring chamber and light waveguide. Here the distance between light waveguide surface and inner peripheral surface of the measuring chamber is kept as small as possible. Advantageously a distance of less than 2 mm, preferably between 0.1–0.05 mm, is to be maintained.

A device according to the invention constructed in this way, such as has been described in the various embodiments, can be made cheaply as a mass product and prepared precoated with appropriate biocomponents. An added advantage lies in that contact of the respective sample liquid with a person is avoided and after carrying out the assay too it is kept securely closed, which is particularly advantageous in medical applications.

For measuring the intensity of fluorescence it is favourable to arrange in the beam path of the light decoupled from the light waveguide a lens and an optical filter permeable to the decoupled fluorescent light in front of the optical detector, wherein the exciting light is blocked by the optical filter. Starting from the lens, the decoupled light is to be directed parallel through the respective filter in a direction towards the optical detector.

In order to get as large a proportion as possible of the decoupled light on the detector, such a lens must be given correspondingly large dimensions.

But as it is disadvantageous to couple the exciting light from the light source through the lens into the light waveguide, it is favourable to provide in the lens a recess by which the exciting light beam from the light source is coupled into the light waveguide without affecting the lens. The better conditions of coupling into the light waveguide that can be attained in this way justify the low loss of decoupled light, which occurs as a result of the recess formed in the lens.

The optical portion of the device according to the invention can be further improved by arranging an additional second lens following the above-mentioned optical filter in the beam path of the decoupled light, with which the fluorescent light conducted through the filter is now focused onto the detector. Here the optical parameters and the distance from the lens to the detector must be selected or adjusted accordingly, so that the image of the fluorescent light decoupled from the light waveguide is imaged on the optical detector.

But it is also possible to focus the light onto the detector with only one lens and a filter in front of the detector. But then this arrangement has a low light intensity.

A particularly favourable development of the invention results with the use of two different light sources with different wavelengths for exciting different labelling substances, so that either two different substances can be measured in parallel or one of the substances serves as a reference substance and so the reliability of the assay result can be greatly increased, so that the demand for internal quality controls can be fulfilled.

If two different light sources are used, naturally two different optical filters are also necessary for the respective fluorescent light. These should advantageously be arranged and capable of being manipulated in such a way that they can be moved alternately into the beam path of the decoupled light, so that it is always only one of the two filters at a time that is located there for the respective fluorescent light.

As the two light sources cannot be arranged at the same location, an additional recess is to be arranged accordingly in the first lens for the second light source, so that its light too impinges directly on the coupling surface of the light waveguide.

It is advantageous on introduction of the corresponding filter into the beam path of the fluorescent light to interrupt the beam path of the other exciting source parallel thereto, so that no light from this source passes into the light waveguide.

It is a further advantageous development of the invention to arrange in front of the detector a stop whose opening can be positioned in the beam path in front of the detector variably in time by translation and/or rotation of the stop. When using a segmented light waveguide, with this arrangement each individual segment of the light waveguide can be measured. It is also favourable to use, instead of one detector, a linear or two-dimensional arrangement of detectors, e.g. a CCD camera, in order to measure the individual segments of the light waveguide.

BRIEF DESCRIPTION OF THE DRAWINGS

Below, the invention will be described in more detail by practical examples. They show.

DESCRIPTION OF THE PREFERRED EMBODIMENT

Figure 1:
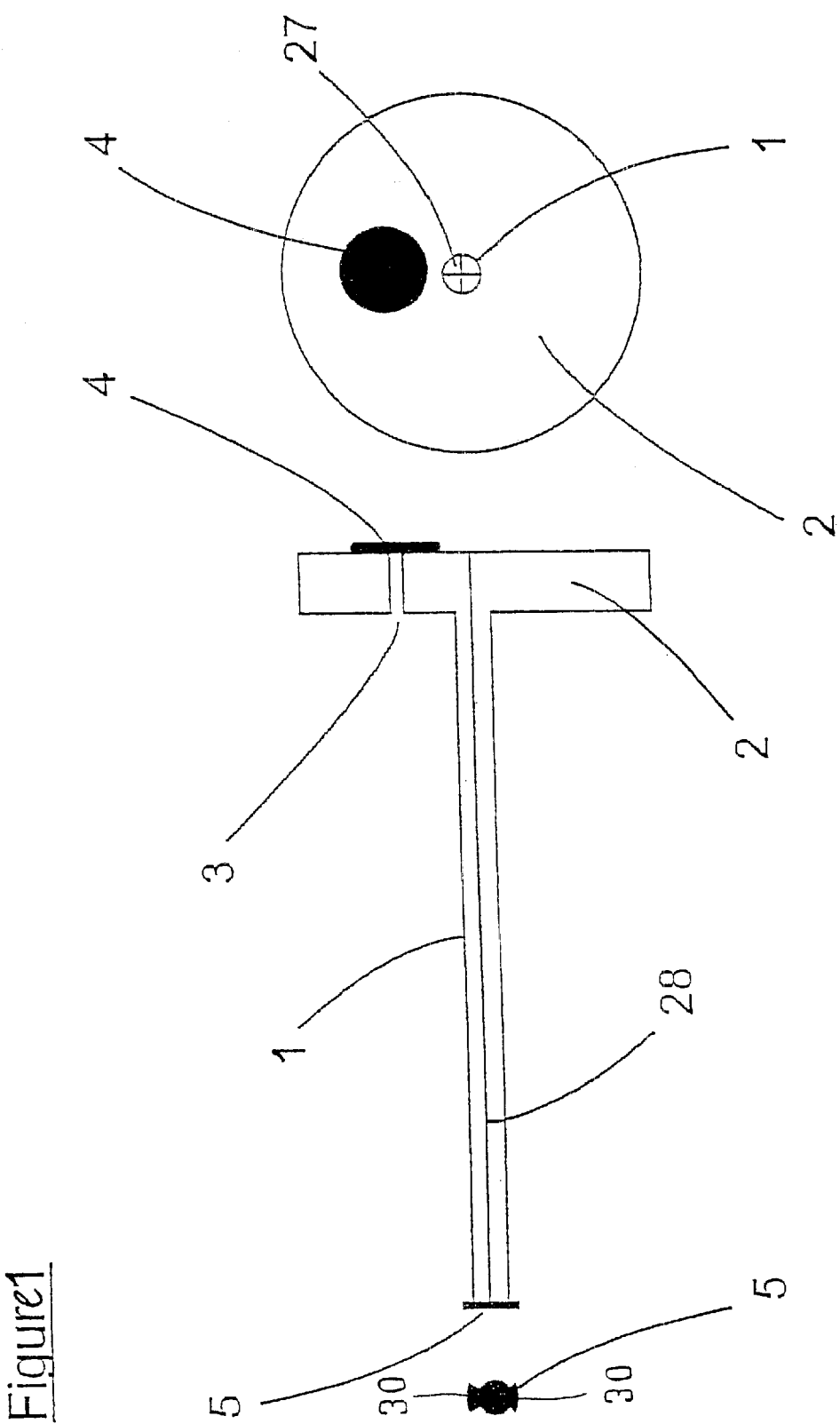
FIG. 1 a light waveguide in several views for a device according to the invention.

In FIG. 1 a light waveguide 1 to be used in a device according to the invention is shown in different views. The light waveguide 1 has at one of its two ends a light absorber 5 made of a dark, preferably black plastic material which absorbs a very large proportion of the incident light. As can moreover be seen in FIG. 1, the light absorber 5 has attachments 30 which allow guiding and fixing on introduction of tie light waveguide 1 into a measuring chamber 9 which will be described in more detail below. It is also possible to mount one or mote such attachments light waveguide 1.

Further, in FIG. 1 is shown one possible manner of division of the light waveguide 1 into several light waveconducting segments 27. The individual segments 27 are here separated from each other by a thin layer 28 whose refractive index $n_2$ is less than that of the light waveconducting segments $n_1$. The side view in FIG. 1 illustrates once again the possible manner shown for dividing the light waveguide 1.

At the other end face of the light waveguide 1 is formed a surface 2 whose diameter is substantially greater than that of the light waveguide 1 and closes one side of a piston 6 also to be described in more detail below, in a direction towards the environment. In the surface 2, in a radially outer region to the light waveguide 1, there is an opening 3 which is temporarily closed with a closure 4. Such a closure can be for example a removable or pierceable film.

The side view shown in FIG. 1 moreover reveals the region of the surface 2 onto which the light is to be directed to excite fluorescence.

Figure 2:
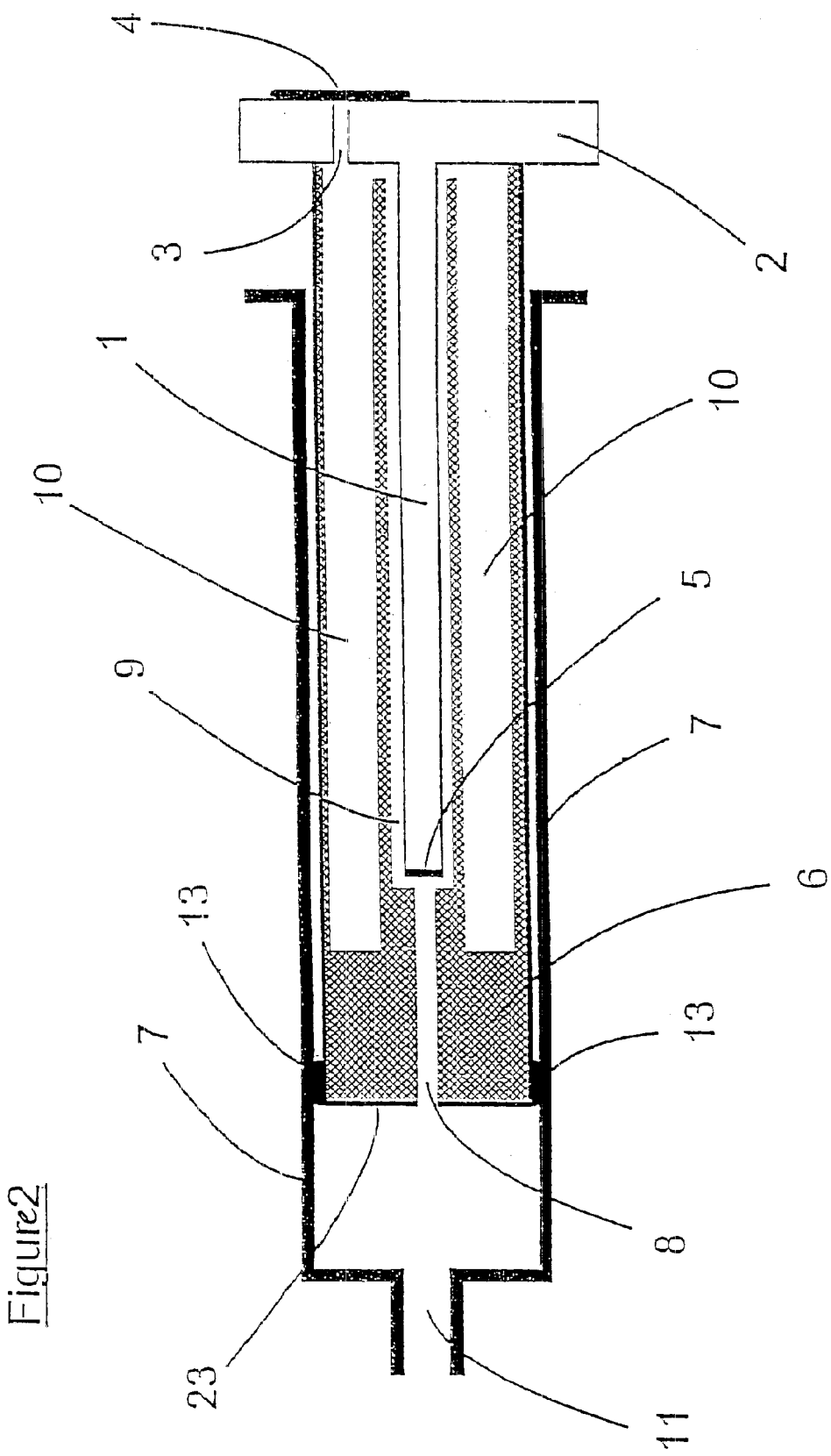
FIG. 2 a device according to the invention in a sectional view.

The light waveguide 1 completed in this way can be introduced into a measuring chamber 9 of a piston 6 and glued with the piston to the surface 2, as can be seen in FIG. 2.

Here a chemical or biochemical component is already immobilised on the surface of the light waveguide 1.

In the piston 6 is moreover formed at least one sample collecting chamber 10 which is connected to the measuring chamber 9, wherein the sample collecting chamber 10 can be constructed in a ring around the measuring chamber 9. The sample collecting chamber 10 should be given dimensions such that it can hold all or a large proportion of the sample liquid volume. In the piston 6 there is an inlet 8 which forms a connection between the measuring chamber 9 and the interior of the cylinder 7 in which the piston 6 has been introduced with the light-waveguide 1. The cylinder 7 has a further inlet 11 through which sample liquid can pass into the interior of the cylinder 7.

If the piston 6 is now moved so that the free interior in the cylinder increases, sample liquid can pass through the inlet 11 into the interior of the cylinder 7, as is also the case with conventional syringes or other piston and cylinder assemblies. As the opening 3 in the surface 2 is closed with the closure 4, no sample liquid can pass through the inlet 8 into the measuring chamber 9. Only at the moment when the opening 3 is at least partially released, can the air contained in the sample collecting chamber 10 and measuring chamber 9 escape and be displaced by the sample liquid which can now pass through the inlet 8, the measuring chamber 9 into the sample collecting chamber 10. Here preferably the cylinder 7 is moved while the piston 6 is fixed, so that the free volume in the interior of the cylinder 7 decreases and, with a given speed of this movement, the corresponding flow rate of the sample liquid through the measuring chamber 9 can also be adjusted in a precise manner. Here outflow of the sample liquid through the inlet 11 should be prevented by means of a valve 15 to be explained further below.

If the sample collecting chamber 10 has a correspondingly large volume, the opening 3 in the surface can be dispensed with. On movement of the cylinder 7, the air in the measuring chamber 9 is displaced by the sample liquid and compressed in the closed sample collecting chamber 10, so that flow through the measuring chamber 9 with the sample liquid is achieved, depending on the direction of movement of the cylinder 7. But even without movement of the cylinder 7 and without a valve 15, sample flow can be effected simply by capillary forces into the measuring chamber 9 and from there into the sample collecting chamber 10 when the closure 4 has been removed or pierced.

Figure 3:
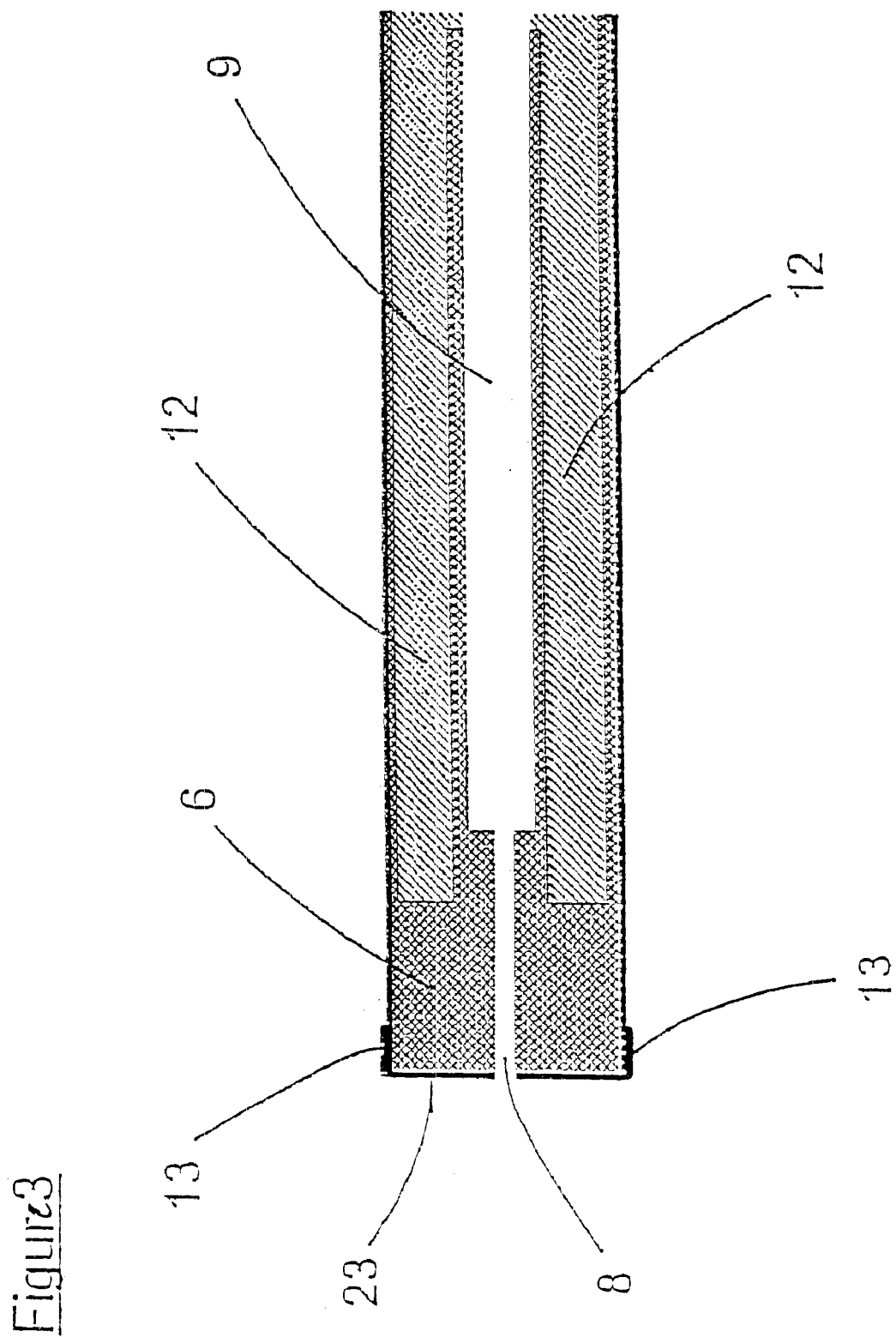
FIG. 3 an example of a piston for a device according to the invention.

In FIG. 3 is shown another example of a piston 6, for a device according to the invention. Here, in this view the piston seal 13 can also be seen clearly.

In this example the sample collecting chamber 10 is filled with a material 12 which is particularly absorbent to the sample liquid, wherein in this view it is not clear that a portion of the absorbent material 12 can extend at least partially into the measuring chamber 9.

With such a design, transport of the sample liquid through the measuring chamber can be assisted by capillary force action of the absorbent material, wherein here too the sample liquid flows through the measuring chamber 9 only when the opening 3 in the surface 2 is at least partially released, and escape of air becomes possible as a result and the inlet 11 is open.

Figure 4:
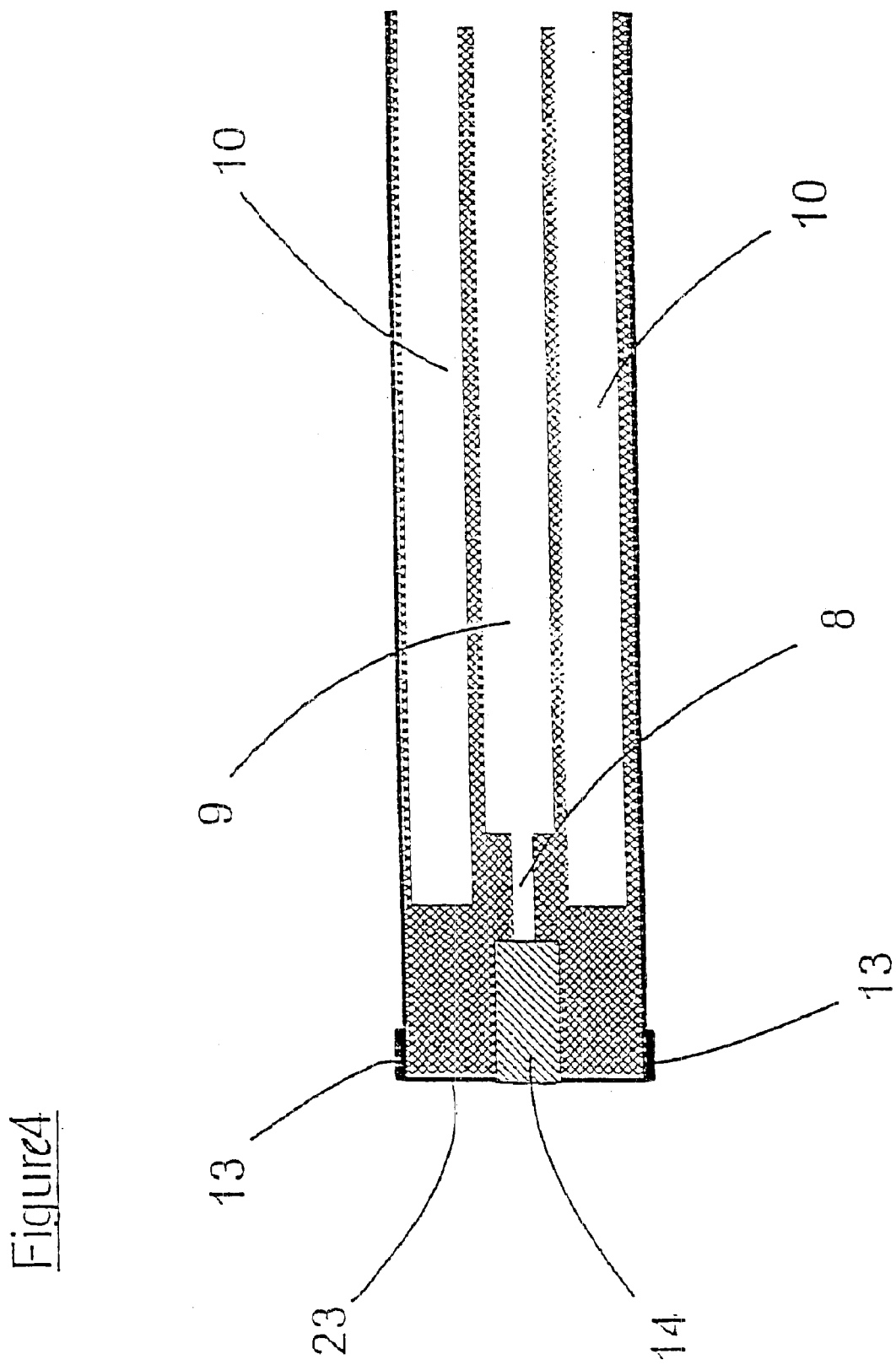
FIG. 4 another example of a piston for a device according to the invention.

In FIG. 4 it is shown that in the inlet 8 of the piston 6 can be arranged a filter or an immunocolumn 14 through which the sample liquid must be passed before actually entering the measuring chamber 9. It is also possible for a filter or membrane to cover the inlet 8 on the piston face 23.

Figure 5:
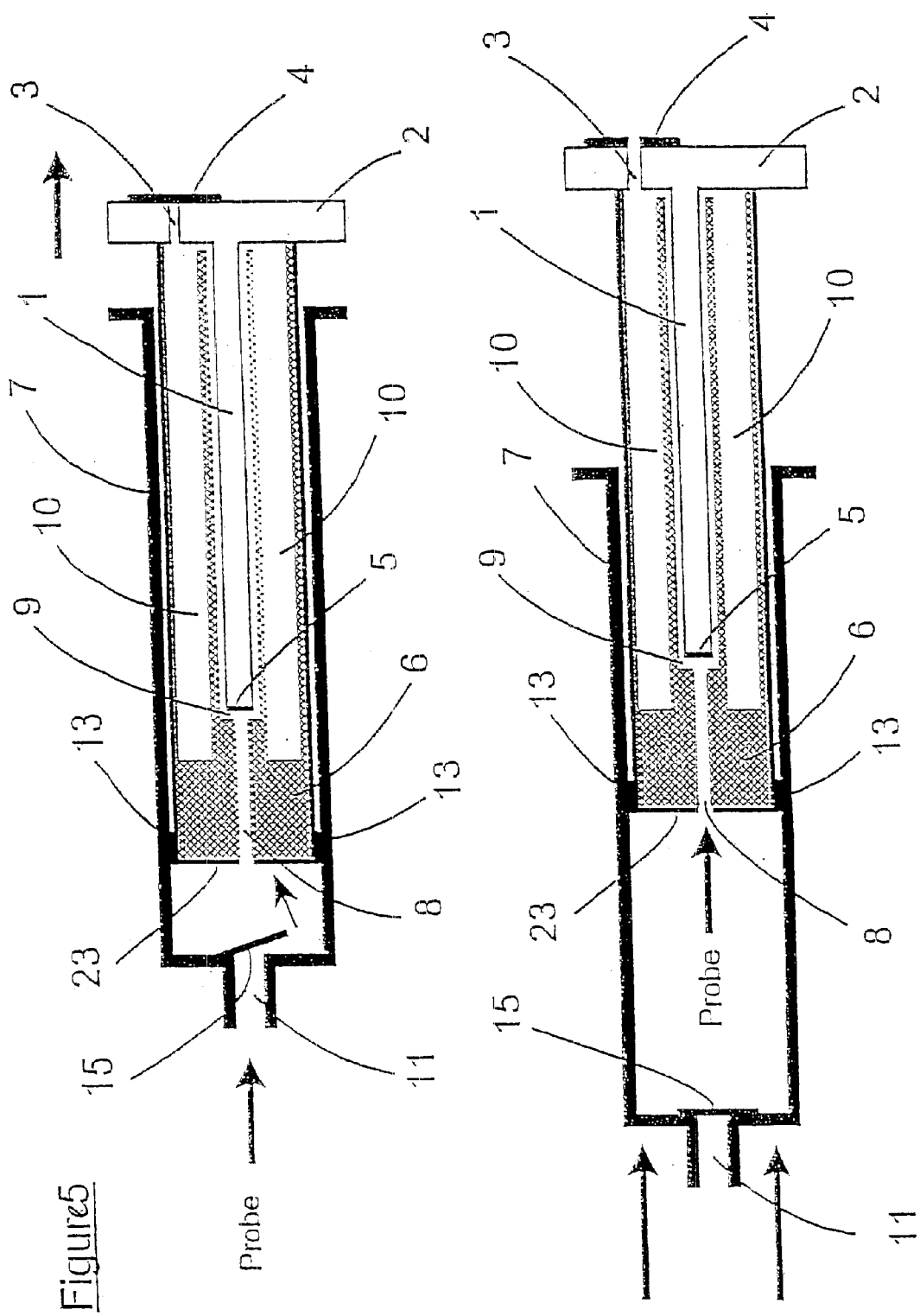
FIG. 5 an example of a device according to the invention with an additional valve in different operating positions, and FIG. 6 an example of the optical portion of a device according to the invention.

In FIG. 5 are shown the arrangement and operation of a valve 15 which blocks or releases the inlet 11 into the interior of the cylinder 7. In this example is used an ordinary flap valve with non-return action which is arranged in the interior of the cylinder 7 in the region of the inlet 11.

If the piston 6 is now moved as made clear with the right arrow, sample liquid can pass through the inlet 11 and the open valve 15 into the interior of the cylinder 7.

When the movement of the piston 6 is over, the valve 15 closes and so prevents sample liquid from undesirably escaping from the interior of the cylinder 7 via the inlet 11.

In this position it can moreover be seen that the closure 4 on the opening 3 is pierced and hence the sample liquid can pass through the inlet 8 into the measuring chamber 9 when, as shown with both arrows in the lower drawing of FIG. 5, the cylinder 7 is moved so that the free interior in the cylinder 7 is decreased and the sample liquid is forced through the inlet 8.

Figure 6:
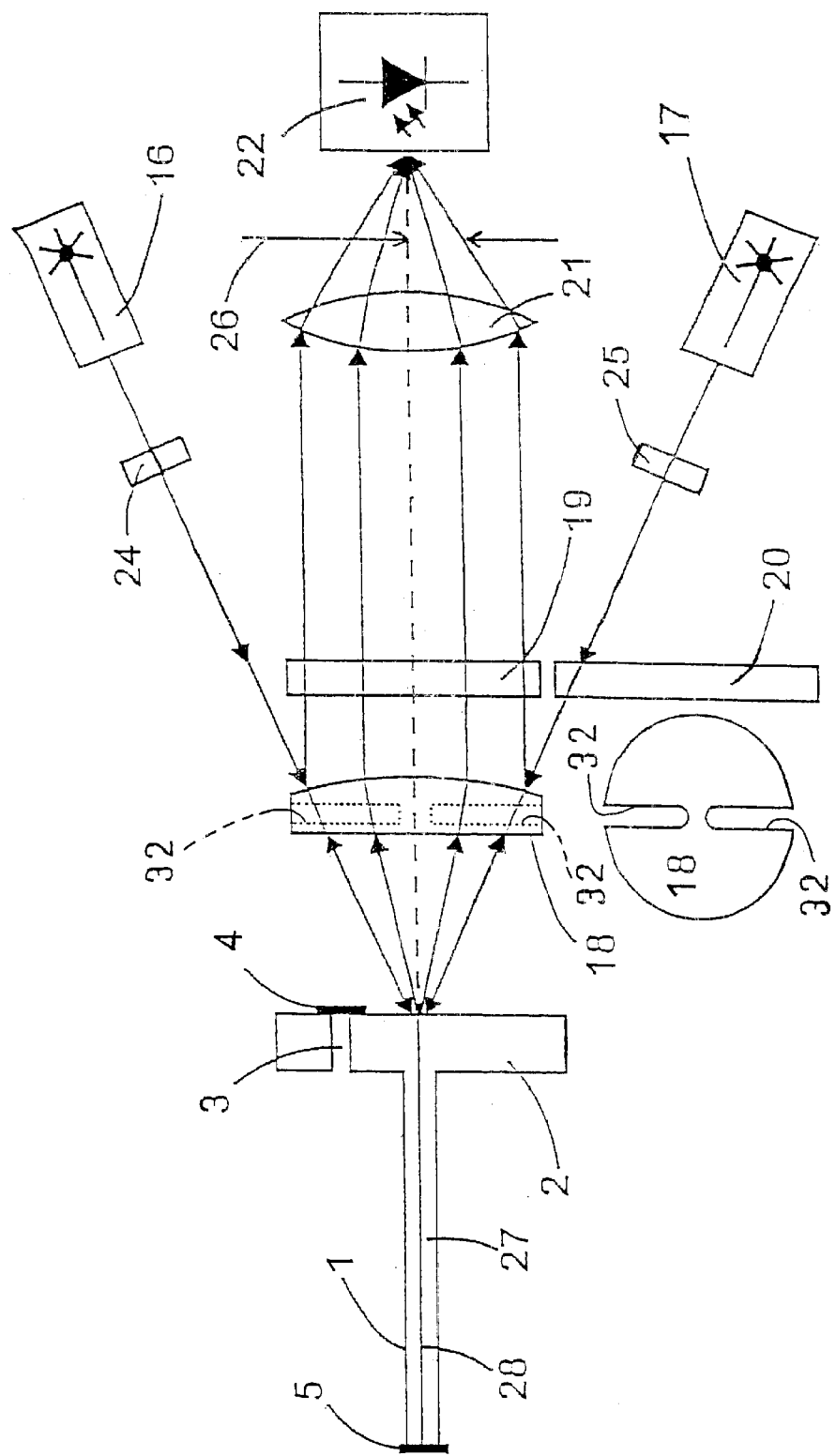

Starting from the lower view in FIG. 5, the sample liquid now flows through the measuring chamber 9 and at the same time the respective fluorescence measurement is performed, wherein the corresponding optical structure can be seen in FIG. 6.

In the example shown there, two laser diodes 16 and 17 are used as light sources in order either to determine two different substances in parallel or to perform a reference measurement in addition.

Here the laser diode 16 directs light onto the coupling surface of the light waveguide 1, at a fixed angle, so that the light for fluorescence excitation is coupled into the light waveguide 1 and guided at a given angle.

In this example there was used a laser diode 16 which emits light at a wavelength with which fluorescence can be excited in the fluorogen Cy5.

The light which is decoupled from the light waveguide 1, and of which a small fraction consists of fluorescent light and a substantially larger fraction consists of backscattered exciting light, passes divergently onto the lens 18 and is directed by means of the lens 18 as a parallel or almost parallel beam through the optical filter 19 in a direction towards the optical detector 22, for measuring the respective intensity of fluorescence. The detector 22 can here be a photodiode, a photoavalanche diode or a photomultiplier.

Here in the beam path in front of the detector is located a filter 19 which is permeable to the fluorescent light of the fluorogen and does not let through the fractions of exciting and scattered light.

The lens 18 is, as can also be seen in FIG. 6, provided with two slot-like recesses 32 by which the exciting light of the laser diodes 16 and 17 can be directed directly onto the coupling surface of the light waveguide 1, without refraction or deflection of the light by the lens 18 occurring.

The laser diode 17 emits light at a wavelength with which the fluorogen Cy7 can be excited.

As the detectable fraction of fluorescent light which can ultimately pass onto the detector 22 is relatively small, it is favourable to move the above-mentioned filter 19 and a second filter 20 which is permeable to fluorescent light of the fluorogen Cy7, alternately into the beam path in front of the detector, and consequently of course also the respective measurement must be made alternately and synchronisation of the measurement signals of the detector 22 with the movement of the two filters 19 and 20 must be performed.

In FIG. 6 it is also shown that an additional lens 21, for focusing the fluorescent light on the detector 22 in the beam path of the light decoupled from the light waveguide 1, is arranged following the filters 19 or 20.

In this example the two laser diodes 16 and 17 are arranged diametrically opposite, but they can also be arranged at almost any other angle to each other.

Here, however, the angle of incidence of the respective light beam of the laser diodes 16 and 17 must be maintained, which can be different in order to ensure almost optimum coupling of the respective exciting light into the light waveguide 1.

As can be seen from FIG. 6, on movement of the filters 19 and/or 20 advantageously the beam path of the light source not needed at the time is also interrupted. Thus e.g. the laser diode 16 and the filter 19 are operated together, while the light of the laser diode 17 cannot pass into the light waveguide 1 because the beam path has been interrupted by the filter 20. The filters 19 and 20 should therefore both be selected so as to be impermeable to light of the laser diodes 16 and 17.

Alternatively to the slots in the lens 18, the diameter of the lens 18 can be decreased so that the light beams of the laser diodes 16 and 17 are not affected by the lens 18, while retaining all set angles.

Moreover in FIG. 6 can also be seen the arrangement of two optical filters 24 and 25 which are arranged directly behind the laser diodes 16 and 17 in the beam path thereof and by which the respective exciting light is filtered according to their design.

In order to direct the light for exciting fluorescence at a fixed and predefined angle onto the coupling surface of the light waveguide 1, the laser diodes 16 and 17 are used as a unit with a corresponding optical system which orients the light beam direction correspondingly parallel.

When using a segmented light waveguide 1, the individual segments 27 can be measured by the fact that in the beam path in front of the detector 22 is located a movable stop 26. The opening of the stop 26 is positioned in the beam path by translation and/or rotation of the stop 26 in such a way that only fluorescent light passes out of a segment 27 of the light waveguide 1 onto the detector 22. As the stop 26 is movable, the fluorescent light from the individual segments 27 can be measured with the detector 22 successively by translation and/or rotation of the stop 26. Also advantageous is the use of a detector 22 which consists of a linear or two-dimensional arrangement of light-sensitive detectors. Thus the fluorescent light from all the segments 27 of the light waveguide 1 can be measured quasi-simultaneously.

What is claimed is:

1. Device for carrying out fluorescence immunoassays comprising:
   at least one light source (16, 17) for emitting light;
   a piston and a cylinder unit, said cylinder unit having a cylinder (7) with a piston (6) disposed therein, wherein at least one of said cylinder (7) and piston (6) moves relative to one another, wherein there is an inlet opening (11) on the cylinder and the inlet opening (11) is closeable with a valve (15);
   a light waveguide (1) having a surface (2) at one end for coupling the light by evanescent field excitation thereat, said piston (6) having a sample collection chamber (10) and a measuring chamber (9) formed ter, said measuring chamber (9) holding the light waveguide (1) therein, said mesas chamber (9) further connected to an interior of the cylinder (7) by an inlet (8) formed in the piston (6) and on the other side of the sample collecting amber (10),
   means for exciting a fluorescence of a labeling substance coupled to one partner of a general receptor ligand system, wherein said partner is bound to a complementary partner immobilized on the surface (2) of the light waveguide (1);
   means for partially coupling fluorescent light into the light waveguide and decoupling the fluorescent light from the light waveguide from the surface of the light waveguide;
   an optical detector (22) for measuring intensity of fluorescent light and;
   an optical system for directing fluorescent light onto the optical detector (22).

2. The device according to claim 1, wherein the light waveguide (1) is divided into at least two light wave-conducting segments (27) parallel to a direction of light propagation in the light waveguide (1) by means of at least one layer (28) whose refractive index $n_2$ is less than the refractive index $n_1$ of the light waveguide material.

3. The device according to claim 1 wherein the measure chamber has an inner peripheral surface and distance between the inner peripheral source of the measuring chamber (9) and the surface of the light waveguide (1) is less than 2 nm.

4. The device according to claim 1 wherein the sample collecting chamber (10) which communicates with the measuring chamber (9) is formed in the piston (6).

5. The device according to claim 1 wherein on the light waveguide (1), for coupling and decoupling light, is formed a surface (2) which closes the piston (6).

6. The device according to claim 5, wherein at an end opposite the surface (2) of the light waveguide (1) for coupling and decoupling light is arranged a light absorber (5).

7. The device according to claim 6, wherein at least on one of the light absorber (5) and on the light waveguide (1) is formed at least one guide attachment.

8. The device according to clam 1, wherein in the surface (2) there is a closable opening (3).

9. The device according to claim 1, wherein a liquid-absorbing material (12) is contained in the sample collecting chamber (10).

10. The device according to claim 1, wherein in or in front of the inlet (8) to the measuring chamber (9) is arranged at least one of a filter, a membrane, and an immunocolumn (14).

11. The device according to claim 1, wherein in a beam path of the light decoupled from the light waveguide (1) are arranged a lens (18) and at least one optical filter (19) permeable to the fluorescent light in front of the optical detector (22).

12. The device according to claim 11, wherein the lens (18) comprises at least one recess by which the light from the light source (16) is directed onto the light waveguide (1).

13. The device according to claim 11, wherein a second light source (17) and a second optical filter (20) are movable alternately with the first optical filter (19) into the beam path of the light decoupled from the light waveguides (1), and the second light source (17) emits light with a wavelength for exciting fluorescence of a second labeling substance.

14. The device according to claim 13, wherein between the first and second optical filter(s) (19, 20) and the detector (22) is arranged a second lens (21).

15. The device according to claim 13, wherein the first and second optical filters are impermeable to light from both light sources (16, 17).

16. The device according to claim 11, wherein in the beam path in front of the detector (22) is arrange a movable stop (26) whose opening is positionable in the beam path variably in time by at least one of translational and rotational movement.

17. The device according to claim 1, wherein the detector (22) is a linear or two-dimsional arrangement of several light-sensitive detectors.

18. The device according to claim 13, wherein in the beam path between the light sources (16, 17) and the surface (2) are arranged optical filters (24, 25).

19. A method for carrying out fluorescence immunoassays comprising the steps of: coupling light from at least one light source (16, 17) into a light waveguide via a surface at one end of the light waveguide (1), and coating the light waveguide (1) with a chemical or biochemical component and introducing the coating into a measuring chamber (9); disposing the measuring chamber with the light waveguide within a cylinder having a piston therein, wherein at least one of said cylinder and piston reciprocally moves relative to each other; conducting sample liquid through ee measuring chamber (9) along the surface of the light waveguide (1) into a sample collecting chamber (10), coupling into the light waveguide simultaneously with excitation of fluorescence with light from the light source (16, 17,) and directing the fluorescent light decoupled from the light waveguide (1) onto an optical detector (22) which measures intensity of the fluorescent light, so that on throughflow of the sample liquid, binding of a fluoresce-labeled component of a general receptor-ligand system to a partner immobilized on the surface of the light waveguide (1) is measured with time resolution, wherein said piston has a piston face and the cylinder has an inlet opening with a surface and at least one of the piston face (23), an inner surface of the cylinder (7), and the surface of the inlet opening 11 is covered with a chemical or biochemical component before carrying out the fluorescence immunoassay, wherein on the light waveguide is formed a surface having a closeable opening for flow of the sample liquid through the measuring chamber (9), the closable opening (3) being at least partially released.

20. A method for carrying out fluorescence immunoassays comprising the steps of: coupling light from at least one light source (16, 17) into a light waveguide via a surface at one end of the light waveguide (1), and coating the light waveguide (1) with a chemical or biochemical component and introducing the coating into a measuring chamber (9); disposing the measuring chamber with the light waveguide within a cylinder having a piston therein, said cylinder and piston reciprocally movable relative to each other; conducting sample liquid through the measuring chamber (9) along the surface of the light waveguide (1) into a sample collecting chamber (10), coupling into the light waveguide simultaneously with excitation of fluorescence with light from the light source (16, 17,) and directing the fluorescent light decoupled from the light waveguides (1) onto an optical detector (22) which measures intensity of the fluorescent light, so that on throughflow of the sample liquid, binding of a fluorescence-labeled component of a general receptor-ligand system to a partner immobilized on the surface of the light waveguide (1) is measured with time resolution, wherein said piston has a piston face and the cylinder has an inlet opening with a surface and at least one of the piston face (23), an inner surface of the cylinder (7), and the surface of the inlet opening (11) is covered with a chemical or biochemical component before carrying out the fluorescence immunoassay, wherein the cylinder has a longitudinal axis and, when the inlet opening at the cylinder (7) is closed, when the opening (3) is closed or in a case of a surface (2) without an opening (3), with the piston (6) fixed and with the surface (2) with light waveguide (1) fixed, the cylinder (7) reciprocally moves parallel to the longitudinal axis of the cylinder, so that the sample liquid flows through the measuring chamber (9) according to the direction of movement of the cylinder (7).

21. The method according to claim 19, wherein with two light sources (16, 17) light for exciting fluorescence of two different labelling substances is coupled into the light waveguide (1) and the decoupled fluorescent light is measured alternately, by corresponding movement of two filters (19, 20) in a beam path of the decoupled light.

22. The method according to claim 21, wherein a second substance in the sample liquid is assayed or a reference measurement is performed.

* * * * *